(12) United States Patent
Ding et al.

(10) Patent No.: US 8,362,313 B2
(45) Date of Patent: Jan. 29, 2013

(54) PROCESSES AND SYSTEMS FOR RECOVERY OF STYRENE FROM A STYRENE-CONTAINING FEEDSTOCK

(75) Inventors: Zhong Yi Ding, Houston, TX (US); Weihua Jin, Houston, TX (US); Andrei Cimpeanu, Houston, TX (US); Amy Sealey, Bozeman, MT (US)

(73) Assignee: GTC Technology, LP, Houston, TX (US)

(*) Notice: Subject to any disclaimer, the term of this patent is extended or adjusted under 35 U.S.C. 154(b) by 504 days.

(21) Appl. No.: 12/697,927

(22) Filed: Feb. 1, 2010

(65) Prior Publication Data
US 2011/0015460 A1    Jan. 20, 2011

Related U.S. Application Data

(60) Provisional application No. 61/226,630, filed on Jul. 17, 2009.

(51) Int. Cl.
*C07C 7/08* (2006.01)
(52) U.S. Cl. ........ 585/806; 585/807; 585/808; 585/833; 585/860
(58) Field of Classification Search .................. None
See application file for complete search history.

(56) References Cited

U.S. PATENT DOCUMENTS

| 3,953,300 A * | 4/1976 | Ginnasi et al. ................. 203/53 |
| 4,031,153 A   | 6/1977 | Haskell |
| 4,039,602 A   | 8/1977 | Uitti |
| 5,877,385 A   | 3/1999 | Lee et al. |
| 7,078,580 B2 * | 7/2006 | Tian et al. ................. 585/833 |
| 7,666,299 B2 * | 2/2010 | Wu et al. ................. 208/313 |
| 7,879,225 B2 * | 2/2011 | Lee et al. ................. 208/313 |

OTHER PUBLICATIONS

Young, Lee W., "International Search Report" for PCT/US10/35888 as mailed Jul. 16, 2010 (2 pages).

* cited by examiner

*Primary Examiner* — Tam M Nguyen
(74) *Attorney, Agent, or Firm* — Winstead PC

(57) ABSTRACT

In various embodiments, the present disclosure describes processes and systems for recovery of styrene from a styrene-rich feedstock. The processes and systems maintain performance of an extractive solvent used in the styrene recovery. In general, the processes include introducing a styrene-rich feedstock to an extractive distillation column, removing a styrene-rich stream from the extractive distillation column, introducing the styrene-rich stream to a solvent recovery column, removing a styrene-lean stream from the solvent recovery column, separating and treating a portion of the styrene-lean stream to form a treated extractive solvent and recycling the treated extractive solvent. In some embodiments, the treating process also includes steam stripping. Styrene-recovery systems including an extractive distillation column, a solvent recovery column, a solvent treatment apparatus having at least one equilibrium stage and a continuous circulation loop connecting these components are also disclosed herein.

17 Claims, 3 Drawing Sheets

PROCESSES AND SYSTEMS FOR RECOVERY OF STYRENE FROM A STYRENE-CONTAINING FEEDSTOCK

CROSS-REFERENCE TO RELATED APPLICATIONS

This application claims priority to U.S. provisional patent application 61/226,630, filed Jul. 17, 2009, which is incorporated by reference herein in its entirety.

STATEMENT REGARDING FEDERALLY SPONSORED RESEARCH

Not applicable.

BACKGROUND

In the course of refining petroleum to produce products such as, for example, fuel, lubricants, and petrochemical compounds, various intermediate and byproduct feedstreams are created. Some of these feedstreams are highly concentrated in $C_8$ hydrocarbons, and some feedstreams, in particular, contain styrene and/or ethylbenzene. Ethylbenzene can be produced by hydrogenation of styrene, and dehydrogenation of ethylbenzene correspondingly produces styrene. Because of its tendency to dimerize and polymerize, styrene is considered to be an unwanted component in feedstreams ultimately intended for fuel use as gasoline. However, styrene is an economically important commodity chemical used in a number of commercial applications such as, for example, as a starting material for making polystyrene. As there is a growing demand for polystyrene-type products, there is accordingly a growing need for styrene raw material.

In view of the foregoing, new methods and systems for separating styrene from a styrene-containing feedstream would be of substantial benefit in the art. In particular, efficient methods and systems to maintain extractive solvent performance in the extractive distillation of styrene from other materials found in pyrolysis gasoline streams would be of specific benefit.

SUMMARY OF THE INVENTION

In various embodiments, processes for recovering styrene and maintaining the performance of an extractive solvent in a system for recovery of styrene from a styrene-rich feedstock are disclosed herein. The processes include a) introducing a styrene-rich feedstock to an extractive distillation column, b) removing a styrene-rich stream comprising styrene and an extractive solvent from the extractive distillation column, c) introducing the styrene-rich stream to a solvent recovery column, d) removing a styrene-lean stream from the solvent recovery column, e) separating a portion of the styrene-lean stream, f) treating the portion of the styrene-lean stream with an organic solvent to form a treated extractive solvent, and g) recycling the treated extractive solvent. In the styrene-lean stream, an amount of styrene is less than amount of styrene in the styrene-rich stream.

In other various embodiments, processes for recovering styrene and maintaining the performance of an extractive solvent in a system for recovery of styrene from a feedstock containing styrene and ethylbenzene are disclosed herein. The methods include a) introducing a feedstock to an extractive distillation column, b) removing a styrene-rich stream comprising styrene and an extractive solvent from the extractive distillation column, c) introducing the styrene-rich stream to a solvent recovery column, d) removing a styrene-lean stream from the solvent recovery column, e) separating a portion of the styrene-lean stream, f) treating the portion of the styrene-lean stream using steam stripping to produce steam-distilled extractive solvent and undistilled extractive solvent, followed by further treating the undistilled extractive solvent with an organic solvent and water wash to form a treated extractive solvent, and g) recycling the distilled extractive solvent. The treated extractive solvent is recirculated to the styrene-lean stream for further steam stripping. In the styrene-lean stream, an amount of styrene is less than amount of styrene in the styrene-rich stream.

In still other various embodiments, styrene-recovery systems are described herein. The styrene-recovery systems include an extractive distillation column, a solvent recovery column, a solvent treatment apparatus having at least one equilibrium stage and a continuous circulation loop connecting the extractive distillation column, the solvent recovery column and the solvent treatment apparatus.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein.

DETAILED DESCRIPTION OF ILLUSTRATIVE EMBODIMENTS

Figure 1:
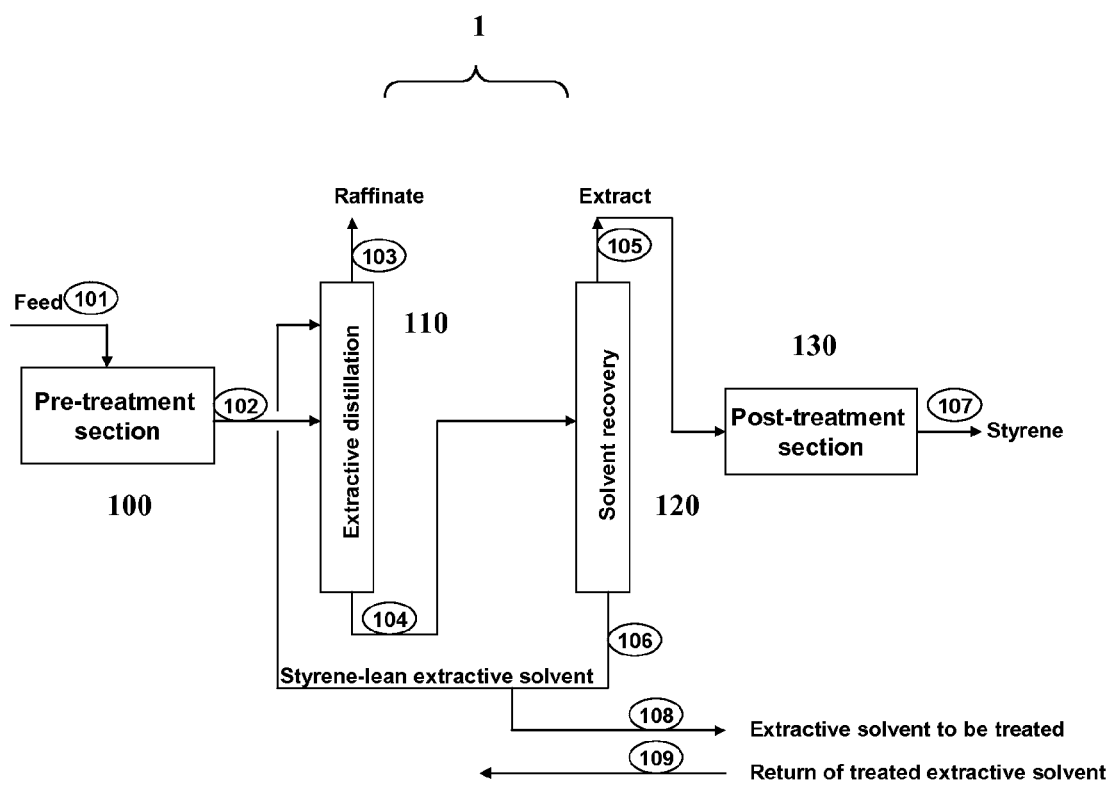
FIG. 1 shows a schematic of an illustrative styrene-recovery system in which styrene is recovered and a styrene-lean extractive solvent is separated to be treated.

In the following description, certain details are set forth such as specific quantities, sizes, etc. so as to provide a thorough understanding of the present embodiments disclosed herein. However, it will be evident to those of ordinary skill in the art that the present disclosure may be practiced without such specific details. In many cases, details concerning such considerations and the like have been omitted inasmuch as such details are not necessary to obtain a complete understanding of the present disclosure and are within the skills of persons of ordinary skill in the relevant art.

Referring to the drawings in general, it will be understood that the illustrations are for the purpose of describing particular embodiments of the disclosure and are not intended to be limiting thereto. Drawings are not necessarily to scale.

While most of the terms used herein will be recognizable to those of ordinary skill in the art, it should be understood, however, that when not explicitly defined, terms should be interpreted as adopting a meaning presently accepted by those of ordinary skill in the art. In cases where the construction of a term would render it meaningless or essentially meaningless, the definition should be taken from Webster's Dictionary, 3rd Edition, 2009. Definitions and/or interpretations should not be incorporated from other patent applications, patents, or publications, related or not, unless specifically stated in this specification or if the incorporation is necessary for maintaining validity.

As used herein, the term "aromatic" refers to aromaticity, a chemical property in which a conjugated ring of unsaturated bonds, lone pairs, or empty orbitals exhibit a stabilization stronger than would be expected by the stabilization of conjugation alone. It can also be considered a manifestation of cyclic delocalization and of resonance stabilization. This is usually considered to be because electrons are free to cycle around circular arrangements of atoms, which are alternately single- and double-bonded to one another.

As used herein, the term "aliphatic" refers to compounds having carbon atoms that are capable of being joined together in straight chains, branched chains, or rings (in which case they are called alicyclic). They can be joined by single bonds (alkanes), double bonds (alkenes), or triple bonds (alkanes).

As used herein, the term "polymer" will collectively refer to polymers of styrene including dimers, trimers, higher styrene oligomers and polymers.

Other than in the operating examples, or where otherwise indicated, all numbers expressing quantities of components used herein are to be understood to be modified in all instances by the term "about".

Various embodiments of the present disclosure are directed toward processes and systems for maintaining extractive solvent performance in producing and/or recovering styrene from various hydrocarbon feedstocks, particularly petroleum feedstocks. As used herein, the term "feedstock" will be understood to include various intermediate streams created during the processing of crude oil or liquid natural gas (LNG) or other mixed hydrocarbons to produce refined petroleum products. Such intermediate streams may include those typically having substantial styrene content such as, for example, pyrolysis gasoline, as well as those typically containing little or no styrene, but containing the related material ethylbenzene, which is readily converted to styrene. An illustrative example of such an intermediate stream containing relatively little styrene is a $C_8$ reformate fraction. According to the embodiments described herein, the methods used to recover styrene and maintain extractive solvent performance include using extractive distillation to recover the styrene from a styrene-rich feedstock.

In various embodiments, processes for recovering styrene and maintaining the performance of an extractive solvent in a system for recovery of styrene from a styrene-rich feedstock are disclosed herein. The processes include a) introducing a styrene-rich feedstock to an extractive distillation column, b) removing a styrene-rich stream comprising styrene and an extractive solvent from the extractive distillation column, c) introducing the styrene-rich stream to a solvent recovery column, d) removing a styrene-lean stream from the solvent recovery column, e) separating a portion of the styrene-lean stream, f) treating the portion of the styrene-lean stream with an organic solvent to form a treated extractive solvent, and g) recycling the treated extractive solvent. In the styrene-lean stream, an amount of styrene is less than amount of styrene in the styrene-rich stream.

In various embodiments, the extractive solvent is a single solvent or a mixture of solvents. In some embodiments, illustrative extractive solvents may include, for example, propylene carbonate, sulfolane (tetramethylene sulfone), methyl carbitol, 1-methyl-2-pyrrolidinone, 2-pyrrolidinone, water and mixtures thereof. As set forth hereinbelow, the extractive solvent may also include a co-solvent.

In various embodiments of the processes described herein, the organic solvent may be, for example, at least one hydrocarbon solvent.

As noted hereinabove, polymerization of styrene is problematic, particularly in gasoline streams. Such polymerization is also problematic in isolating styrene for use in industrial applications. In various embodiments of the present disclosure, a portion of a styrene-lean stream containing residual styrene and an extractive solvent is treated to remove polymers of styrene. Such treatment is advantageous in balancing and/or adjusting the formation rate of polymer in an extractive distillation solvent loop, as described herein, and counterbalancing the formation rate with that of removal rate produced by treatment of the extractive solvent. By removing unwanted styrene polymers, the performance of extractive solvent is maintained throughout the run time of the extractive distillation process.

In various embodiments, the step of treating the styrene-lean stream further includes washing the styrene-lean stream with water. In some embodiments, a ratio of the water to the extractive solvent is from about 4 to about 0.2. In some embodiments, a ratio of the water to the extractive solvent is from about 2 to about 0.5. In other embodiments, a ratio of the water to the extractive solvent is from about 1 to about 0.001. In still other embodiments, a ratio of the water to the extractive solvent is from about 0.5 to about 0.01. In still other embodiments, a ratio of the water to the extractive solvent is from about 0.1 to about 0.01.

In some embodiments, the styrene-lean stream includes about 0 to about 40% extractive solvent. In some other embodiments, the styrene-lean stream includes about 0 to about 10% extractive solvent. The referenced percentages are relative to the total volume of extractive solvent.

In some embodiments, the styrene-lean stream is washed with the water and the organic solvent at the same time. However, in other embodiments, the styrene-lean stream is mixed with the organic solvent and then mixed with the water in the treating step. The step of mixing the organic solvent and the water may be reversed in an embodiment. Such staged washing steps are advantageous when the extractive solvent in the styrene-lean stream has a preferential solubility in one of the organic solvent and the water. Such washing steps of the styrene-lean stream at least partially minimizes the accumulation of polymer in the extractive solvent upon recycling of the extractive solvent in a continuous solvent loop. In various embodiments, the removal of polymer results in increased consistency, performance and reproducibility of the extractive distillation processes for recovering styrene described herein.

In some embodiments described herein, the step of treating the styrene-lean stream takes place in a liquid-liquid equilibrium system having at least one equilibrium stage. An equilibrium stage may include a mixer, separator or like instrument for affecting a phase separation. In some embodiments, the liquid-liquid equilibrium system has one equilibrium stage. However, in other embodiments, liquid-liquid equilibrium systems having two, three, four, five, six, seven or more equilibrium stages may be used within the spirit and scope of the present disclosure. In some embodiments, there are up to seven equilibrium stages. An illustrative liquid-liquid equilibrium system having five equilibrium stages is shown hereinbelow in FIG. 2.

In some embodiments, after treating the styrene-lean stream, the extractive solvent is collected by distillation. In other various embodiments, the extractive solvent is recycled back to the extractive distillation column used in the extractive distillation apparatus for further recovery of styrene from a styrene-containing feedstream. In some embodiments, the recycling takes place through a continuous loop. In some embodiments, at least a portion of the water in the extractive solvent after treatment is separated before the extractive solvent is recycled back to the extractive distillation column of the extractive distillation system.

In further embodiments of the present disclosure, methods for minimizing the accumulation of process chemicals (other than polymer) and/or the like in the extractive solvent are described herein. Such process chemicals include, for example, inhibitors, retarders, and/or the like that are used in prevention of polymer formation and/or styrene formation. Contaminants that can be removed by the various processes and systems of the present disclosure include, for example, chemicals for preventing corrosion, emulsion and/or the like.

In other various embodiments of the present disclosure, processes for recovering styrene and maintaining the performance of an extractive solvent in a system for recovery of styrene from a feedstock containing styrene and ethylbenzene are disclosed herein. The methods include a) introducing a feedstock to an extractive distillation column, b) removing a styrene-rich stream comprising styrene and an extractive solvent from the extractive distillation column, c) introducing the styrene-rich stream to a solvent recovery column, d) removing a styrene-lean stream from the solvent recovery column, e) separating a portion of the styrene-lean stream, f) treating the portion of the styrene-lean stream using steam stripping to produce steam-distilled extractive solvent and undistilled extractive solvent, followed by further treating the undistilled extractive solvent with an organic solvent and water wash to form a treated extractive solvent, and g) recycling the distilled extractive solvent. The treated extractive solvent is recirculated to the styrene-lean stream for further steam stripping. In the styrene-lean stream, an amount of styrene is less than amount of styrene in the styrene-rich stream.

In some embodiments, steam stripping includes using a steam stripping column to separate the extractive solvent from the styrene-lean stream. For example, a portion of styrene-lean stream is sent/conveyed through a steam stripping column and at least a portion of the extractive solvent is recovered by distillation. That portion of the extractive solvent that does not distill (i.e., undistilled extractive solvent) may be further treated with an organic solvent and water wash which takes place in a liquid-liquid equilibrium system having at least one equilibrium stage. Such a styrene-recovery system having a steam stripping column and liquid-liquid equilibrium system is described hereinbelow. In various embodiments, the extractive solvent is recycled after being distilled.

In still further embodiments of the present disclosure, the performance of the extractive solvent is maintained or enhanced by adding at least one co-solvent to the extractive solvent. In an embodiment, the co-solvent enhances polymer solubility in extractive solvent. Accordingly, the volume of extractive solvent needed to remove a given amount of polymer is reduced. In various embodiments, the co-solvent may be, for example, co-boiling aromatic compounds and glycol ethers (e.g., ethylene glycol ethers and propylene glycol ethers).

The extractive distillation techniques described herein advantageously maintain performance of an extractive solvent used in styrene recovery. Furthermore, the methods are advantageous in that they allow recovery of not only styrene but also ethylbenzene, which may be subsequently converted to yield additional styrene. Pre-processing and post-processing steps that may be used in the processes described herein to accomplish such separation include, for example and without limitation, hydrogenation, dehydrogenation, splitting of the extractive solvent prior to or after the extractive distillation steps, and splitting of the extractive solvent during the extractive distillation steps.

Extractive distillation techniques employing further processing steps may be used for recovering styrene from a feedstream containing at least styrene, ethylbenzene, and, optionally, one or more aromatic or non-aromatic hydrocarbon compounds. The processes include separating the feedstream into a first stream relatively more concentrated in styrene than the feedstream (e.g., a styrene-rich stream) and a second stream relatively more concentrated in ethylbenzene than the feedstream (e.g., a styrene-poor stream), recovering styrene from the first stream, dehydrogenating the ethylbenzene of the second stream to produce additional styrene, and recovering the additional styrene.

Embodiments of the present disclosure will now be described in further detail by referring to the drawings. FIG. 1 shows a schematic of an illustrative styrene-recovery system 1 in which styrene is recovered and a styrene-lean extractive solvent is separated to be treated. As shown in FIG. 1, a styrene-containing feed is fed through line 101 into pre-treatment section 100 to form a styrene-rich feedstream which exits through line 102. For example, in an embodiment, pyrolysis gasoline is fed through line 101, and one or more sequentially arranged fractionation columns in pre-treatment section 100 performs a tight separation of styrene-rich $C_8$ fractions to form a styrene-rich feedstream which exits through line 102. In some embodiments, pre-treatment section 100 may also include a hydrogenator to selectively hydrogenate any acetylenic compounds such as, for example, phenylacetylene, without converting a significant portion of styrene to ethylbenzene.

Still referring to FIG. 1, the styrene-rich feedstream flows into extractive distillation column 110. Styrene-lean extractive solvent is introduced to extractive distillation column 110 through line 106. In an embodiment, extractive distillation column 110 may have secondary solvent entering the column as described in U.S. Pat. No. 5,877,385, the contents of which are hereby incorporated by reference in their entirety. A styrene-lean raffinate stream exits extractive distillation column 110 through overhead line 103. A styrene-rich stream exits extractive distillation column 110 through bottom line 104 and is fed to solvent recovery column 120, where the separation of styrene from the extractive solvent is performed. Crude styrene leaves solvent recovery column 120 through overhead line 105 and subsequently enters post-treatment section 130 to purify the styrene to required product specifications. Post-treatment section 130 may include, but is not limited to, a drier system, a color and sulfur removal system, and a finish distillation column. Purified styrene exits post-treatment section 130 through line 107.

A styrene-lean stream exits solvent recovery column 120 through bottom line 106. In an embodiment, bottom line 106 may pass a series of heat exchangers to recover energy from the stream before the styrene-lean stream is fed back to extractive distillation column 110. As part of the continuous flow apparatus shown in FIG. 1, a portion of the styrene-lean stream is continuously removed for treatment of the extractive solvent. The location to take out this portion of the styrene-lean stream could be at the outlet of the solvent recovery column 130 or between and after the heat exchangers described hereinabove. As described herein, continual treatment of the styrene-lean stream maintains performance of the extractive solvent for extractive distillation of styrene.

Referring still to FIG. 1, the portion of the styrene-lean stream passes through line 108 for treatment and returns through line 109 after being treated. In some embodiments, the portion of the styrene-lean stream removed ranges from about 0 to about 40% of the total circulation extractive solvent. In other embodiments, the portion of the styrene-lean stream removed ranges from about 0 to about 20% of the total extractive solvent. In still other embodiments, the portion of the styrene-lean stream removed ranges from about 0 to about 10% of the total extractive solvent.

Figure 2:
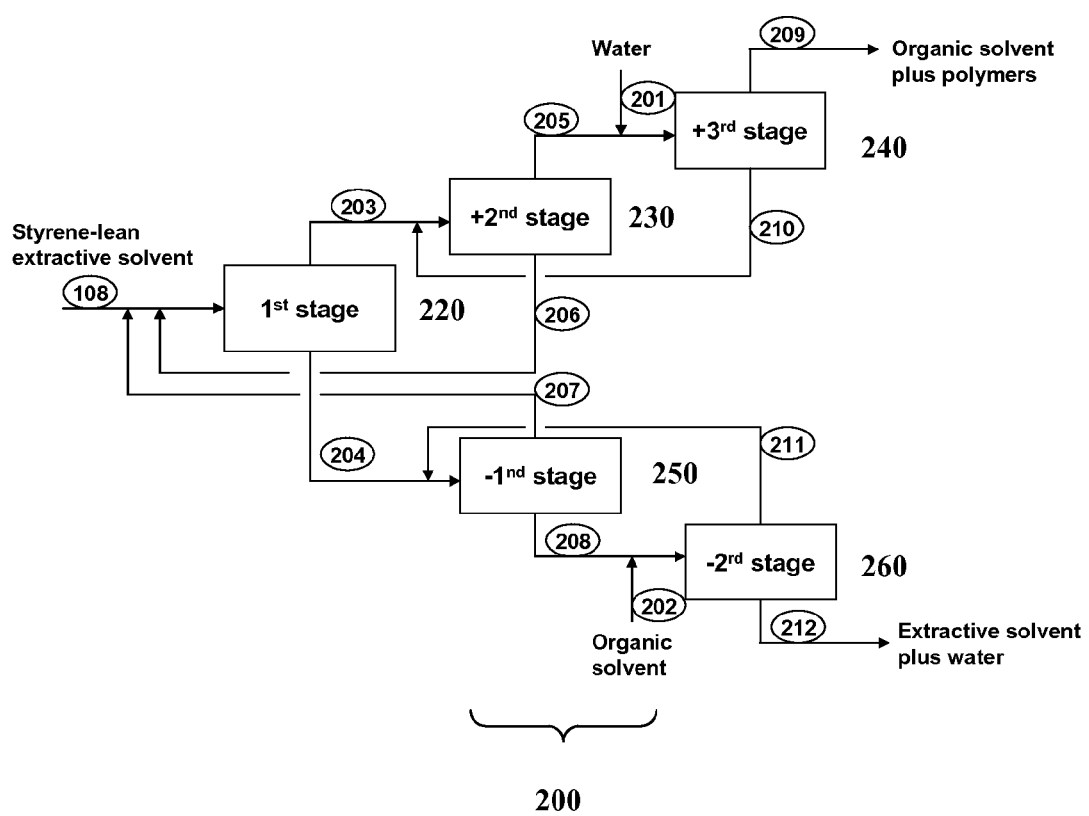
FIG. 2 shows a schematic of an illustrative multiple-stage apparatus for treating a styrene-lean stream.

FIG. 2 shows a schematic of an illustrative multiple-stage apparatus 200 for treating a styrene-lean stream. A styrene-lean stream flows into multi-stage apparatus 200 through line 108 (see FIG. 1) and enters $1^{st}$ stage equilibrium system 220. Multi-stage apparatus 200 may include horizontal and vertical tanks, as well as a multi-stage liquid-liquid extraction columns. The styrene-lean stream contacts organic solvent and water either before or while entering the 1st equilibrium system 220 and further mixing takes place therein, in an embodiment. In an embodiment, the styrene-lean phase is first mixed with an organic solvent before being mixed with water. Upon adding water, two phases will exist in the 1st equilibrium system 220, a light organic phase containing a majority of the organic solvent and polymer and a heavy organic phase containing water and extractive solvent. Light organic phase exits 1st equilibrium system 220 through line 203 and the heavy organic phase exits through line 204. The light organic phase can be washed with water supplied through line 201 in further equilibrium systems 230 (+2nd stage) and 240 (+3rd stage) to further reduce the content of the extractive solvent content in the organic phase. For example, after further equilibrium system 230, light organic phase exits through line 205 and enters further equilibrium system 240, and heavy organic phase exits through line 206 and is returned to 1st equilibrium system 220. Likewise, after further equilibrium system 240, light organic phase exits multiple-stage apparatus 200 through line 209 and heavy organic phase exits through line 210 and is returned to further equilibrium system 230. The aqueous phase from +3rd stage (i.e., 240) is fed to +2nd stage (i.e., 230) and then to 1st stage (i.e., 220). There is no limitation of stages/systems that can be used, and a skillful person can configure more stages than those shown in FIG. 2 while operating within the sprit and scope of the present disclosure.

In a similar manner, the heavy organic phase containing water removed through line 204 may be flowed to further equilibrium systems 250 and 260 in order to reduce polymer content in the heavy organic phase (e.g., extractive solvent plus water). As shown in FIG. 2, fresh organic solvent enters multiple-stage apparatus 200 through line 202. Heavy organic phase enters further equilibrium system 250, and light organic phase is removed through line 207 and returned to equilibrium system 220. Heavy organic phase exits further equilibrium system 250 through line 208 and enters further equilibrium system 260. In a like manner, light organic phase is removed through line 211 and is returned to further equilibrium system 250. Heavy organic phase exits further equilibrium system 260 through line 211 and is ready to be returned to the styrene recovery system 1 as illustrated in FIG. 1. The heavy organic phase exiting through line 212 (i.e., extractive solvent plus water stream) can be optionally treated to reduce water content or be sent directly to styrene recovery system 1.

The stages to complete the treatment of the extractive solvent could be arranged in −2nd stage to +5th stage in some embodiments, in −1st stage to +2nd stage in other embodiments, and from a 1st stage to +2nd stage in still other embodiments.

In further embodiments, the organic solvent removed through line 209 may contain other process chemicals. These process chemicals can include, without limitation, inhibitor and retarder compounds used in prevention of polymer formation, as well as chemicals for preventing corrosion, emulsion and the like.

Figure 3:
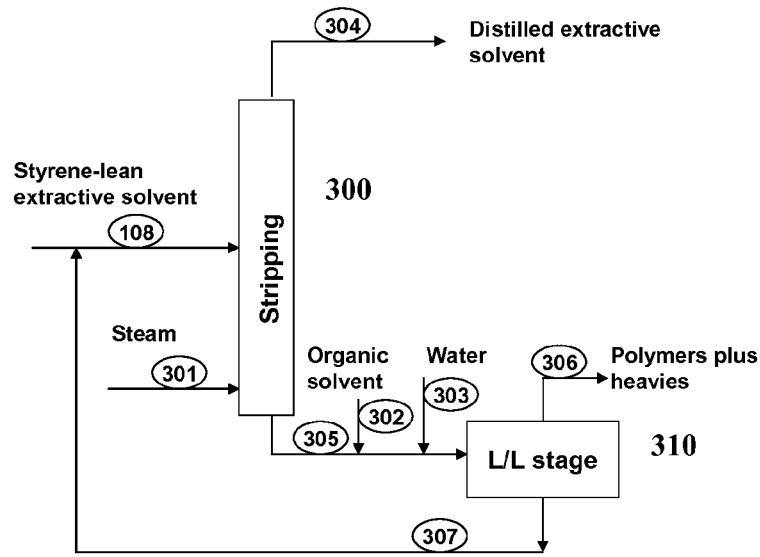
FIG. 3 shows a schematic of an illustrative styrene-recovery system in which styrene is separated and a styrene-lean stream is treated using a steam stripping column; and, FIG. 4 shows a schematic of an illustrative styrene-recovery system in which a co-solvent is added to the extractive solvent to aid in the styrene recovery process.

FIG. 3 shows a schematic of an illustrative styrene-recovery system in which styrene is separated and a styrene-lean stream is treated using a steam stripping column 300. In the embodiment shown in FIG. 3, the styrene-lean stream from line 108 (see FIG. 1) is sent to stripping column 300, where steam from line 301 is used to strip the extractive solvent. The overhead stream exiting from line 304 and containing extractive solvent can be sent directly to the extractive distillation system used in the styrene recovery process. The bottom stream exiting through line 305 can optionally have a one stage liquid-liquid wash performed in liquid/liquid washing stage 310 with organic solvent supplied through line 302 and water supplied through line 303. Liquid-liquid extraction is performed in a like manner to that described in the embodiment of FIG. 2. The organic phase from liquid/liquid washing stage 310 is removed through line 306 and discarded or sent for further solvent recycling. Aqueous phase exiting through line 307 is mixed with styrene-lean stream in line 108 and sent back to the stripping column 300. The stripping column 300 accomplished separation of the majority of the extractive solvent from polymers, heavy organics and inorganic materials. Since the majority of the extractive solvent is removed from stripping column 300 through line 304, a one stage liquid-liquid washing is generally sufficient to recover the remaining extractive solvent in the aqueous phase recovered from the bottoms of the stripping column 300. However, it will be evident to one having ordinary skill in the art the additional liquid-liquid washing may be performed if deemed necessary.

Figure 4:
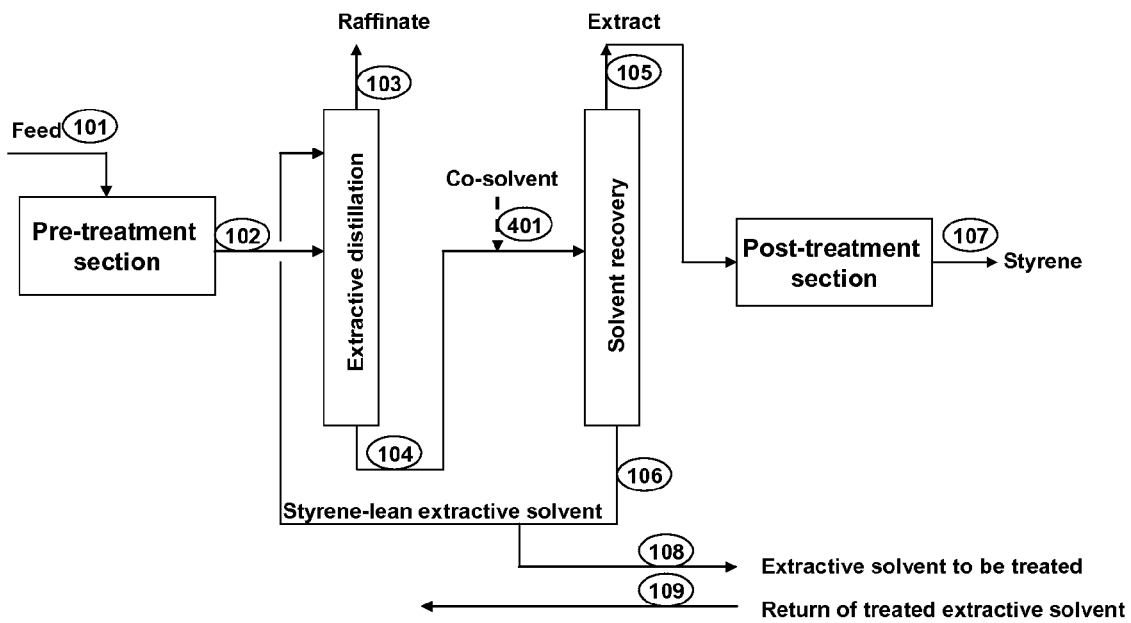

FIG. 4 shows a schematic of an illustrative styrene-recovery system in which a co-solvent is added to the extractive solvent to aid in the styrene recovery process. As shown in FIG. 4, a co-solvent is added to the embodiment of the styrene-recovery system of FIG. 1 through line 401. Co-solvent can be added either continuously or periodically to the extractive solvent circulation loop defined by styrene-recovery system 1. In an embodiment, the co-solvent has a boiling point that is identical or nearly identical to that of the extractive solvent. In other embodiments, the co-solvent has a co-boiling point with that of the extractive solvent. In this embodiment, a co-boiling point is defined a boiling point which is closer to that of the extractive solvent than to that of styrene. Hence, with a co-boiling solvent, the majority of co-solvent will stay with extractive solvent in the extractive distillation and solvent recovery columns. In an embodiment, addition of the co-solvent may benefit one of the functions of extractive solvent such as, for example, capacity of the extractive solvent toward styrene and polymer and selectivity of solvency. In some embodiments, the co-solvent can be, for example, co-boiling aromatic compounds, glycol ethers, and combinations thereof.

In accordance with the various embodiments described hereinabove, the present disclosure also describes styrene-recovery systems having an extractive distillation column, a solvent recovery column, a solvent treatment apparatus having at least one equilibrium stage and a continuous circulation loop connecting the extractive distillation column, the solvent recovery column and the solvent treatment apparatus. In some embodiments, the styrene-recovery systems further include a steam stripping column that is also part of the continuous circulation loop. In some other embodiments, the styrene-recovery systems further include a co-solvent injection line connected to the continuous circulation loop.

It should be appreciated by those of ordinary skill in the art that the techniques and embodiments disclosed hereinabove are merely illustrative modes for practice of the disclosure. Those of ordinary skill in the art should, in light of the present disclosure, appreciate that many changes can be made in the specific embodiments that are disclosed and still obtain a like or similar result without departing from the spirit and scope of the disclosure.

From the foregoing description, one of ordinary skill in the art can easily ascertain the essential characteristics of this disclosure, and without departing from the spirit and scope thereof, can make various changes and modifications to adapt the disclosure to various usages and conditions. The embodiments described hereinabove are meant to be illustrative only and should not be taken as limiting of the scope of the disclosure, which is defined in the following claims.

What is claimed is the following:

1. A process for recovering styrene and maintaining performance of an extractive solvent in a system for recovery of styrene from a styrene-rich feedstock, said process comprising the steps of:
   (a) introducing the styrene-rich feedstock to an extractive distillation column;
   (b) removing a styrene-rich stream from the extractive distillation column;
      wherein the styrene-rich stream comprises styrene and the extractive solvent;
   (c) introducing the styrene-rich stream to a solvent recovery column;
   (d) removing a styrene-lean stream from the solvent recovery column;
      wherein an amount of styrene in the styrene-lean stream is less than an amount of styrene in the styrene-rich stream;
   (e) separating a portion of the styrene-lean stream;
   (f) treating the portion of the styrene-lean stream with an organic solvent to form a treated extractive solvent; and,
   (g) recycling the treated extractive solvent.

2. The process of claim 1, wherein the treating step further comprises washing the styrene-lean stream with water.

3. The process of claim 2, wherein a ratio of the water to the extractive solvent is about 4 to about 0.2.

4. The process of claim 1, wherein the extractive solvent comprises about 0 to about 40% of the styrene-lean stream.

5. The process of claim 1, wherein the extractive solvent comprises about 0 to about 10% of the styrene-lean stream.

6. The process of claim 1, wherein the treating step takes place in a liquid-liquid equilibrium system comprising at least one equilibrium stage.

7. The process of claim 6, wherein there are up to seven equilibrium stages.

8. The process of claim 1, wherein the organic solvent comprises at least one hydrocarbon.

9. The process of claim 1, wherein the treating step comprises mixing the styrene-lean stream with the organic solvent and then mixing with water.

10. The process of claim 1, further comprising:
   adding at least one co-solvent to the extractive solvent.

11. The process of claim 10, wherein the at least one co-solvent is selected from the group consisting of co-boiling aromatic compounds and glycol ethers.

12. A process for recovering styrene and maintaining performance of an extractive solvent in a system for recovery of styrene from a feedstock comprising styrene and ethylbenzene, said process comprising the steps of:
   (a) introducing the feedstock to an extractive distillation column;
   (b) removing a styrene-rich stream from the extractive distillation column;
      wherein the styrene-rich stream comprises styrene and the extractive solvent;
   (c) introducing the styrene-rich stream to a solvent recovery column;
   (d) removing a styrene-lean stream from the solvent recovery column;
      wherein an amount of styrene in the styrene-lean stream is less than an amount of styrene in the styrene-rich stream;
   (e) separating a portion of the styrene-lean stream;
   (f) treating the portion of the styrene-lean stream using steam stripping to produce steam-distilled extractive solvent and undistilled extractive solvent;
      wherein undistilled extractive solvent is further treated with an organic solvent and water wash to form a treated extractive solvent; and
      wherein the treated extractive solvent is recirculated to the styrene-lean stream for further steam stripping; and
   (g) recycling the distilled extractive solvent.

13. The process of claim 12, wherein the extractive solvent comprises about 0 to about 40% of the styrene-lean stream.

14. The process of claim 12, wherein the steam stripping comprises using a steam stripping column to separate the extractive solvent from the styrene-lean stream.

15. The process of claim 12, wherein the step of treating the undistilled extractive solvent with an organic solvent and water wash takes place in a liquid-liquid equilibrium system comprising at least one equilibrium stage.

16. The process of claim 12, further comprising:
   adding at least one co-solvent to the extractive solvent.

17. The process of claim 16, wherein the at least one co-solvent is selected from the group consisting of co-boiling aromatic compounds and glycol ethers.

* * * * *

UNITED STATES PATENT AND TRADEMARK OFFICE
CERTIFICATE OF CORRECTION

PATENT NO. : 8,362,313 B2
APPLICATION NO. : 12/697927
DATED : January 29, 2013
INVENTOR(S) : Zhongyi Ding et al.

It is certified that error appears in the above-identified patent and that said Letters Patent is hereby corrected as shown below:

In the Specification

Column 3, Line 21

Replace "triple bonds (alkanes)."

With -- triple bonds (alkynes). --

Signed and Sealed this
Seventh Day of May, 2013

Teresa Stanek Rea
*Acting Director of the United States Patent and Trademark Office*